United States Patent
Collier et al.

(10) Patent No.: US 9,650,551 B2
(45) Date of Patent: May 16, 2017

(54) COMPOSITION INCLUDING 2,3,3,3-TETRAFLUOROPROPENE

(71) Applicant: ARKEMA FRANCE, Colombes (FR)

(72) Inventors: Bertrand Collier, Saint Genis Laval (FR); Dominique Deur-Bert, Charly (FR); Laurent Wendlinger, Soucieu en Jarrest (FR)

(73) Assignee: ARKEMA FRANCE, Colombes (FR)

( * ) Notice: Subject to any disclaimer, the term of this patent is extended or adjusted under 35 U.S.C. 154(b) by 7 days.

(21) Appl. No.: 14/651,855

(22) PCT Filed: Dec. 6, 2013

(86) PCT No.: PCT/FR2013/052977
§ 371 (c)(1),
(2) Date: Jun. 12, 2015

(87) PCT Pub. No.: WO2014/102479
PCT Pub. Date: Jul. 3, 2014

(65) Prior Publication Data
US 2015/0322317 A1    Nov. 12, 2015

(30) Foreign Application Priority Data
Dec. 26, 2012 (FR) ...................... 12 62766

(51) Int. Cl.
*C09K 5/04* (2006.01)
*C09K 3/00* (2006.01)
*H01B 3/56* (2006.01)

(52) U.S. Cl.
CPC ............ *C09K 3/00* (2013.01); *C09K 5/044* (2013.01); *C09K 5/045* (2013.01); *H01B 3/56* (2013.01);
(Continued)

(58) Field of Classification Search
CPC ............... C09K 2205/16; C09K 5/044; C09K 2205/122
See application file for complete search history.

(56) References Cited

U.S. PATENT DOCUMENTS 2,931,840 A * 4/1960 Marquis ............... C07C 17/269
526/252
8,070,977 B2   12/2011 Rached
(Continued)

FOREIGN PATENT DOCUMENTS

WO    WO 2012/098420 A1    7/2012

OTHER PUBLICATIONS

International Search Report (PCT/ISA/210) mailed on Apr. 9, 2014, by the Japanese Patent Office as the International Searching Authority for International Application No. PCT/FR2013/052977.
(Continued)

*Primary Examiner* — John Hardee
(74) *Attorney, Agent, or Firm* — Buchanan Ingersoll & Rooney P.C.

(57) ABSTRACT

A composition including the compound HFO-1234yf and at least one other, additional, compound selected from HCFC-240db, HCFO-1233xf, HCFC-243db, HCFO-1233zd, HCC-40, HCFC-114a, HCFC-115, HCFC-122, HCFC-23, HCFC-124, HCFC-124a, HFC-125, HCFC-133a, HCFC-142, HCFC-143, HFC-52a, HCFC-243ab, HCFC-244eb, HFC-281ea, HCO-1110, HCFO-1111, HCFO-1113, HCFO-1223xd, and HCFO-1224xe. A composition including the compound HFO-1234yf and at least two compounds selected from HFO-1234ze, HFC-245cb, HFC-134a, HCFC-115, HFC-152a, HCC-40 and HFO-1243zf.

13 Claims, 1 Drawing Sheet

(52) U.S. Cl.
CPC .. *C09K 2205/122* (2013.01); *C09K 2205/126* (2013.01); *C09K 2205/22* (2013.01); *C09K 2205/32* (2013.01)

(56) References Cited

U.S. PATENT DOCUMENTS

| | | |
|---|---|---|
| 8,075,798 B2 | 12/2011 | Rached |
| 8,246,850 B2 | 8/2012 | Rached |
| 8,252,198 B2 | 8/2012 | Rached |
| 8,557,135 B2 | 10/2013 | Rached |
| 8,808,569 B2 | 8/2014 | Rached |
| 8,858,824 B2 | 10/2014 | Boussand |
| 8,858,825 B2 | 10/2014 | Guerin et al. |
| 9,011,711 B2 | 4/2015 | Rached |
| 9,028,706 B2 | 5/2015 | Rached et al. |
| 9,039,922 B2 | 5/2015 | Rached |
| 9,127,191 B2 | 9/2015 | Rached |
| 9,133,379 B2 | 9/2015 | Rached |
| 9,175,203 B2 | 11/2015 | Rached |
| 9,267,064 B2 | 2/2016 | Rached |
| 9,315,708 B2 | 4/2016 | Guerin et al. |
| 9,399,726 B2 | 7/2016 | Rached |
| 9,599,381 B2 | 3/2017 | Rached |
| 2007/0112227 A1 | 5/2007 | Mukhopadhyay et al. |
| 2007/0112229 A1 | 5/2007 | Mukhopadhyay et al. |
| 2009/0253946 A1* | 10/2009 | Van Der Puy ........ C07C 17/206 570/159 |
| 2011/0031436 A1 | 2/2011 | Mahler et al. |
| 2011/0084228 A1 | 4/2011 | Rached |
| 2011/0095224 A1 | 4/2011 | Rached |
| 2011/0105809 A1* | 5/2011 | Devic ................... C07C 17/389 570/179 |
| 2011/0186772 A1 | 8/2011 | Rached |
| 2011/0219791 A1 | 9/2011 | Rached |
| 2011/0219792 A1 | 9/2011 | Rached |
| 2011/0240254 A1 | 10/2011 | Rached |
| 2011/0284181 A1 | 11/2011 | Rached |
| 2012/0049104 A1 | 3/2012 | Rached |
| 2012/0056123 A1 | 3/2012 | Rached |
| 2012/0068105 A1 | 3/2012 | Rached et al. |
| 2012/0144857 A1 | 6/2012 | Rached |
| 2012/0151958 A1 | 6/2012 | Rached |
| 2012/0151959 A1 | 6/2012 | Rached |
| 2012/0153213 A1 | 6/2012 | Rached |
| 2012/0159982 A1 | 6/2012 | Rached |
| 2012/0161064 A1 | 6/2012 | Rached |
| 2012/0167615 A1 | 7/2012 | Rached |
| 2012/0205574 A1 | 8/2012 | Rached et al. |
| 2013/0092869 A1 | 4/2013 | Boussand |
| 2013/0105724 A1 | 5/2013 | Boussand |
| 2013/0186114 A1 | 7/2013 | Guerin et al. |
| 2014/0008565 A1 | 1/2014 | Rached et al. |
| 2014/0031597 A1 | 1/2014 | Deur-Bert et al. |
| 2014/0075969 A1 | 3/2014 | Guerin et al. |
| 2014/0318160 A1 | 10/2014 | Rached |
| 2014/0326017 A1 | 11/2014 | Rached |
| 2015/0027146 A1 | 1/2015 | Boussand |
| 2015/0152306 A1 | 6/2015 | Rached |
| 2015/0152307 A1 | 6/2015 | Rached |
| 2015/0322321 A1 | 11/2015 | Deur-Bert et al. |
| 2015/0344761 A1 | 12/2015 | Rached |
| 2015/0353799 A1 | 12/2015 | Deur-Bert et al. |
| 2015/0353802 A1 | 12/2015 | Rached |
| 2016/0009555 A1 | 1/2016 | Bonnet et al. |
| 2016/0024363 A1 | 1/2016 | Rached |
| 2016/0025394 A1 | 1/2016 | Rached |
| 2016/0115361 A1 | 4/2016 | Boussand |
| 2016/0122609 A1 | 5/2016 | Rached |
| 2016/0194541 A1 | 7/2016 | Guerin et al. |
| 2016/0244652 A1 | 8/2016 | Rached |
| 2016/0272561 A1 | 9/2016 | Rached et al. |
| 2016/0298014 A1 | 10/2016 | Rached |
| 2016/0376484 A1 | 12/2016 | Guerin et al. |
| 2017/0037291 A1 | 2/2017 | Rached et al. |
| 2017/0080773 A1 | 3/2017 | Rached |

OTHER PUBLICATIONS

U.S. Appl. No. 14/651,925, filed Jun. 12, 2015, Dominique Deur-Bert and Laurent Wendlinger.
U.S. Appl. No. 14/655,500, filed Jun. 25, 2015, Dominique Deur-Bert and Laurent Wendlinger.
U.S. Appl. No. 14/823,430, filed Aug. 11, 2015, Wissam Rached.
U.S. Appl. No. 14/830,130, filed Aug. 19, 2015, Wissam Rached.
U.S. Appl. No. 14/772,950, filed Sep. 4, 2015, Phillippe Bonnet, Bertrand Collier, Dominique Deur-Bert, and Laurent Wendlinger.
U.S. Appl. No. 14/873,855, filed Oct. 2, 2015, Wissam Rached.
U.S. Appl. No. 14/873,891, filed Oct. 2, 2015, Wissam Rached.
U.S. Appl. No. 14/903,461, filed Jan. 7, 2016, Sophie Guerin and Wissam Rached.
U.S. Appl. No. 14/990,159, filed Jan. 7, 2016, Béatrice Boussand.
U.S. Appl. No. 14/992,387, filed Jan. 11, 2016, Wissam Rached.
U.S. Appl. No. 15/070,955, filed Mar. 15, 2016, Sophie Guerin, Laurent Abbas and Wissam Rached.
U.S. Appl. No. 15/073,108, filed Mar. 17, 2016, Wissam Rached, Sophie Guerin and Pascale Kindler.
Guerin, Sophie, et al., U.S. Appl. No. 14/903,461, entitled, "2,3,3,3-Tetrafluoropropene Compositions Having improved Miscibility," filed in the U.S. Patent and Trademark Office on Jan. 7, 2016.
Boussand, Beatrice, et al., U.S. Appl. No. 14/990,159, entitled "Stable 2,3,3,3-Tetrafluoropropene Composition," filed in the U.S. Patent and Trademark office on Jan. 7, 2016
Rached, Wissam, U.S. Appl. No. 14/992,387 entitled, "Ternary Compositions for High-Capacity Refrigeration," filed in the U.S. Patent and Trademark Office on Jan. 11, 2016.
Guerin, Sophie, et al., U.S. Appl. No. 15/070,955, entitled "Heat-Transfer Compositions Exhibiting Improved Miscibility with the Lubricating Oil," filed in the U.S. Patent and Trademark Office Mar. 15, 2016.
Rached, Wissam, et al., U.S. Appl. No. 15/073,108 entitled "Stabilization of 1-Chloro-3,3,3-Trifluoropropene," filed in the U.S. Patent and Trademark Office on Mar. 17, 2016.
U.S. Appl. No. 15/238,883, filed Aug. 17, 2016, Wissam Rached.
U.S. Appl. No. 15/297,569, filed Oct. 19, 2016, Wissam Rached.
Rached, Wissam, U.S. Appl. No. 15/238,883 enlitled "Heat Transfer Fluid Replacing R-134a," filed in the U.S. Patent and Trademark Office on Aug, 17 2016.
Rached, Wissam, et al., U.S. Appl. No. 15/297,569 entitled "Composition Based on 2,3,3,3-Tetrafluoropropene," filed in the U.S. Patent and Trademark Office on Oct. 19, 2016.
Deur-Bert, Dominique, et al., U.S. Appl. No. 14/651,925 entitled "Composition Containing 2,3,3,3-Tetrafluoropropene and 1,2-Difluoroethylene," filed in the U.S. Patent and Trademark Office on Jun. 12, 2015.
Deur-Bert, Dominique, el al., U.S. Appl. No. 14/655,500 entitled "Azeotropic or Quasi-Azeotropic Composition of Chloromethane," filed in the U.S. Patent and Trademark Office on Jun. 25, 2015.
Rached, Wissam, U.S. Appl. No. 14/823,430 entitled "Use of Ternary Compositions," filed in the U.S. Patent and Trademark Office on Aug. 11, 2015.
Rached, Wissam, U.S. Appl. No. 14/830,130 entitled "Binary Refrigerating Fluid," filed in the U.S. Patent and Trademark Office on Aug. 19, 2015.
Bonnet, Phillippe, et al., U.S. Appl. No. 14/772,950 entitled "Composition Comprising HF and 2,3,3,3-Tetrafluoropropene," filed in the U.S. Patent and Trademark Office on Sep. 4, 2015.
Rached, Wissam, U.S. Appl. No. 14/873,855 entitled "Heat Transfer Fluid," filed in the U.S. Patent and Trademark Office on Oct. 2, 2015.
Rached, Wissam, U.S. Appl. No. 14/873,891 entitled "Ternary Compositions for Low-Capacity Refrigeration," filed in the U.S. Patent and Trademark Office on Oct. 2, 2015.
Rached, Wissam, U.S. Appl. No. 15/396,855 entitled "Heat Transfer Fluid," filed in the U.S. Patent and Trademark Office on Jan. 3, 2017.

* cited by examiner

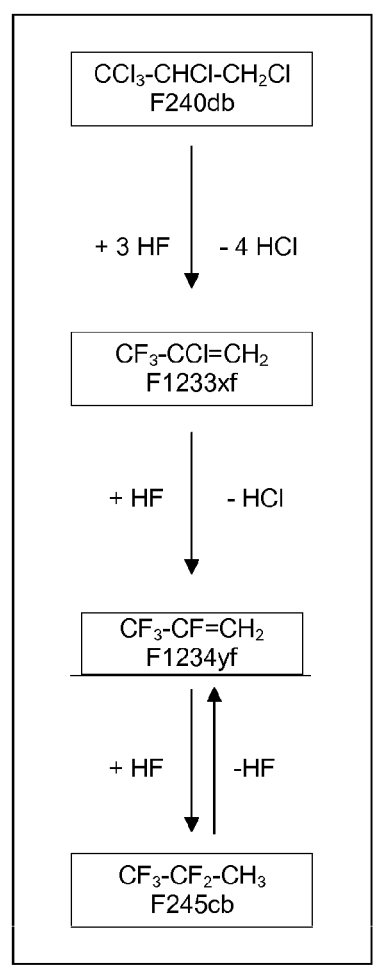

COMPOSITION INCLUDING 2,3,3,3-TETRAFLUOROPROPENE

The present invention relates to compositions comprising 2,3,3,3-tetrafluoropropene, which are of use in many fields of application such as refrigeration, blowing agents, solvents and aerosols.

One very important parameter in the choice of a composition of use in the fields of refrigeration, air conditioning and heat pumps is its impact on the environment.

The manufacture of 2,3,3,3-tetrafluoropropene (HFO-1234yf), being accompanied by a multitude of by-products having a boiling point close to HFO-1234yf, results in quite complex and expensive purification steps. The difficulty encountered during the purification of HFO-1234yf generally involves a consequent loss of desired product. Furthermore, these by-products may form binary or tertiary azeotropic compositions with HFO-1234yf, rendering the separation by simple distillation impossible.

One subject of the present invention is a composition comprising the compound HFO-1234yf and at least one other additional compound chosen from HCFC-240db, HCFO-1233xf, HCFC-243db, HCFO-1233zd, HCC-40, HCFC-114a, HCFC-115, HCFC-122, HCFC-123, HCFC-124, HCFC-124a, HFC-125, HCFC-133a, HCFC-142, HCFC-143, HFC-152a, HCFC-243ab, HCFC-244eb, HFC-281ea, HCO-1110, HCFO-1111, HCFO-1113, HCFO-1223xd and HCFO-1224xe.

Preferably, all of the additional compounds represents at most 1% by weight of the composition comprising the HFO-1234yf and advantageously at most 0.5% by weight.

Compounds such as HCFC-115, HFC-152a and HCC-40 have a boiling point particularly close to that of HFO-1234yf.

According to one embodiment of the invention, the composition comprises the compound HFO-1234yf and at least one other additional compound chosen from HCFC-115, HFC-152a and HCC-40, preferably HFC-152a and/or HCC-40.

Advantageously, the HCFC-115 and/or HFC-152a and/or HCC-40 when it (they) is (are) present in the composition, represent(s) at most 500 ppm and particularly preferably represent(s) at most 50 ppm.

According to this embodiment, the composition may additionally comprise at least one compound chosen from HCFC-240db, HCFO-1233xf, HCFC-243db, HCFO-1233zd, HCFC-114a, HCFC-122, HCFC-123, HCFC-124, HCFC-124a, HFC-125, HCFC-133a, HCFC-142, HCFC-143, HCFC-243ab, HCFC-244eb, HFC-281ea, HCO-1110, HCFO-1111, HCFO-1113, HCFO-1223xd and HCFO-1224xe.

In one embodiment, the composition according to the invention may also comprise at least one compound chosen from HFO-1234ze, HFC-245cb, HFC-245eb, HFC-245fa, HFC-23, HFC-134a, HFC-143a, HFC-236fa, HCFC-244bb, HCFC-244db, HFO-1132a, HFO-1223, HFO-1225zc, HFO-1225ye, HCFO-1232xf and HFO-1243zf.

Irrespective of the embodiment, all of the additional compound(s) represents at most 1% by weight of the composition comprising the HFO-1234yf and advantageously at most 0.5% by weight.

By way of example, mention may especially be made of the following compounds, the acronyms of which represent:

HCFC-240db: 1,1,1,2,3-pentachloropropane or $CCl_3$—$CHCl$—$CH_2Cl$

HCFO-1233xf: 3,3,3-trifluoro-2-chloropropene or $CF_3$—$CCl$=$CH_2$

HCFC-243db: 1,1,1-trifluoro-2,3-dichloropropane or $CF_3$—$CHCl$—$CH_2Cl$

HCFO-1233zd: E/Z-3,3,3-trifluoro-1-chloropropene or $CF_3$—$CH$=$CHCl$

HCC-40: chloromethane or $CH_3Cl$

HCFC-114a: 1,1,1,2-tetrafluoro-2,2-dichloroethane or $CF_3$—$CCl_2F$

HCFC-115: 1,1,1,2,2-pentafluoro-2-chloroethane $CF_3$—$CClF_2$

HCFC-122: 1,1,2-trichloro-2,2-difluoroethane or $CHCl_2$—$CClF_2$

HCFC-123: 1,1,1-trifluoro-2,2-dichloroethane or $CF_3$—$CHCl_2$

HCFC-124: 1,1,1,2-tetrafluoro-2-chloroethane or $CF_3$—$CHClF$

HCFC-124a: 1,1,2,2,-tetrafluoro-2-chloroethane or $CHF_2$—$CClF_2$

HFC-125: 1,1,1,2,2,-pentafluoroethane or $CF_3$—$CHF_2$

HCFC-133a: 1,1,1-trifluoro-2-chloroethane or $CF_3$—$CH_2Cl$

HCFC-142: 1,1-difluoro-2-chloroethane or $CHF_2$—$CH_2Cl$

HCFC-143: 1,1,2-trifluoroethane or $CHF_2$—$CH_2F$

HFC-152a: 1,1-difluoroethane or $CHF_2$—$CH_3$

HCFC-243ab: 1,1,1-trifluoro-2,2-dichloropropane or $CF_3$—$CCl_2$—$CH_3$

HCFC-244eb: 1,1,1,2-tetrafluoro-3-chloropropane or $CF_3$—$CHF$—$CH_2Cl$

HFC-281ea: 2-fluoropropane or $CH_3$—$CFH$—$CH_3$

HCO-1110: 1,1,2,2-tetrachloroethylene or $CCl_2$=$CCl_2$

HCFO-1111: 1,1,2-trichloro-2-fluoroethylene or $CCl_2$=$CClF$

HCFO-1113: 1,1,2-trifluoro-2-chloroethylene or $CF_2$=$CClF$

HCFO-1223xd: E/Z-3,3,3-trifluoro-1,2-dichloropropene or $CF_3$—$CCl$=$CHCl$

HCFO-1224xe: E/Z-1,3,3,3-tetrafluoro-2-chloropropene or $CF_3$—$CCl$=$CHF$

HFO-1234ze: E/Z-1,3,3,3-tetrafluoropropene or $CF_3$—$CH$=$CHF$

HFC-245cb: 1,1,1,2,2-pentafluoropropane or $CF_3$—$CF_2$—$CH_3$

HFC-245eb: 1,1,1,2,3-pentafluoropropane or $CF_3$—$CHF$—$CH_2F$

HFC-245fa: 1,1,1,3,3-pentafluoropropane or $CF_3$—$CH_2$—$CHF_2$

HFC-23: trifluoromethane or $CHF_3$

HFC-134a: 1,1,1,2-tetrafluoroethane or $CF_3$—$CH_2F$

HFC-143a: 1,1,1-trifluoroethane or $CF_3$—$CH_3$

HFC-236fa: 1,1,1,3,3,3-hexafluoropropane or $CF_3$—$CH_2$—$CF_3$

HCFC-244bb: 1,1,1,2-tetrafluoro-2-chloropropane or $CF_3$—$CFCl$—$CH_3$

HCFC-244db: 1,1,1,3-tetrafluoro-2-chloropropane or $CF_3$—$CHCl$—$CH_2F$

HFO-1132a: 1,2-difluoroethylene or $CHF$=$CHF$

HFO-1223: 3,3,3-trifluoropropyne or $CF_3$—$C$≡$CH$

HFO-1225zc: E/Z-1,1,3,3,3-pentafluoropropene or $CF_3$—$CH$=$CF_2$

HFO-1225ye: E/Z-1,2,3,3,3-pentafluoropropene or $CF_3$—$CF$=$CHF$

HCFO-1232xf: 3,3-difluoro-1,3-dichloropropene or $CClF_2$—$CCl$=$CH_2$

HFO-1243zf: 3,3,3-trifluoropropene or $CF_3$—$CH$=$CH_2$

According to one more particular embodiment, the composition according to the invention may comprise a ternary mixture, for example a mixture chosen from:

HFO-1234yf, HFC-152a, HFC-245cb
HFO-1234yf, HCC-40, HFC-245cb
HFO-1234yf, HCFC-115, HFC-245cb
HFO-1234yf, HFC-152a, HFC-134a
HFO-1234yf, HCC-40, HFC-134a
HFO-1234yf, HCFC-115, HFC-134a
HFO-1234yf, HFC-152a, HFO-1234ze
HFO-1234yf, HCC-40, HFO-1234ze
HFO-1234yf, HCFC-115, HFO-1234ze
HFO-1234yf, HCC-40, HFC-152a
HFO-1234yf, HCC-40, HCFC-115
HFO-1234yf, HFC-134a, HFO-1234ze
HFO-1234yf, HFC-134a, HFO-1243zf
HFO-1234yf, HFO-1234ze, HFC-134a
HFO-1234yf, HFO-1234ze, HFC-245cb
HFO-1234yf, HFO-1243zf, HFC-245cb
HFO-1234yf, HFO-1243zf, HFC-152a
HFO-1234yf, HFO-1243zf, HCFC-115

According to one more particular embodiment, the composition according to the invention may comprise a quaternary mixture, for example a mixture chosen from:

HFO-1234yf, HFC-152a, HCC-40, HFC-245cb
HFO-1234yf, HFC-152a, HCC-40, HFC-1234ze

It would not be outside the scope of the invention if the composition comprises a mixture of more than four compounds.

Another subject of the present invention is a composition comprising the compound HFO-1234yf and at least two compounds chosen from HFO-1234ze, HFC-245cb, HFC-134a, HCFC-115, HFC-152a, HCC-40 and HFO-1243zf.

Preferably, the composition comprises the compound HFO-1234yf, HCC-40 and at least one compound chosen from HFO-1234ze, HFC-134a, HCFC-115, HFC-152a and HFO-1243zf.

Preferably, the composition comprises the compound HFO-1234yf, HFC-134a and at least one compound chosen from HFO-1234ze, HCFC-115, HFC-152a and HFO-1243zf.

Preferably, the composition comprises the compound HFO-1234yf, HFO-1234ze and at least one compound chosen from HFC-245cb, HCFC-115, HFC-152a and HFO-1243zf.

Preferably, the composition comprises the compound HFO-1234yf, HFO-1243zf and at least one compound chosen from HFC-245cb, HCFC-115 and HFC-152a.

The preferred and/or aforementioned compositions may additionally comprise at least one other additional compound chosen from HCFC-240db, HCFO-1233xf, HCFC-243db, HCFO-1233zd, HCFC-114a, HCFC-122, HCFC-123, HCFC-124, HCFC-124a, HFC-125, HCFC-133a, HCFC-142, HCFC-143, HCFC-243ab, HCFC-244eb, HFC-281ea, HCO-1110, HCFO-1111, HCFO-1113, HCFO-1223xd, HFC-245eb, HFC-245fa, HFC-23, HFC-143a, HFC-236fa, HCFC-244bb, HCFC-244db, HFO-1132a, HFO-1223, HFO-1225zc, HFO-1225ye, HCFO-1232xf and HCFO-1224xe.

Irrespective of the embodiment, the compound HFO-1234yf preferably represents at least 99% by weight in the composition and advantageously at least 99.5% by weight.

The composition according to the invention may be obtained from HCC-240db and by using one or more reaction steps.

Thus, HCC-240db may be subjected to a gas-phase reaction step with a fluorinating agent, preferably anhydrous HF, in order to directly give HFO-1234yf, optionally accompanied by intermediate products chosen from HCFO-1233xf, HCFC-243db and HCFO-1233zd. The fluorination reaction may be carried out in the presence of a catalyst and preferably at a temperature between 100° C. and 500° C., more preferably between 200° C. and 450° C. After separation of the HFO-1234yf, in particular by settling followed by distillation, the intermediate product(s) and where appropriate the unreacted HCC-240db may then be recycled to the reaction step.

The composition according to the invention may also be obtained from HCC-240db by means of at least two reaction steps. The first step generally consists in subjecting the HCC-240db to a gas-phase reaction with a fluorinating agent, preferably anhydrous HF, in order to give at least one intermediate product such as HCFO-1233xf. In a second step, the intermediate product reacts with a fluorinating agent, preferably anhydrous HF, in order to give a composition comprising HFO-1234yf and at least one additional compound as described above. At the end of the second step, the composition comprising the HFO-1234yf and at least one additional compound is subjected to a separation and/or purification step.

The two steps may be carried out in the presence of a catalyst, it being possible for the catalyst to be identical or different. These steps may be carried out in one and the same reactor when the reaction is carried out in the gas phase. In this case, the reactor may comprise an upper catalyst bed different from that of the lower bed.

When the preparation is carried out using two reactions steps, the reaction temperature of the first step is generally lower than that of the second step and is preferably between 100° C. and 500° C., more preferably between 200° C. and 450° C.

If necessary, after the aforementioned separation and/or purification step, the stream comprising HFO-1234yf may be subjected to a step of azeotropic distillation and/or of adsorption by activated carbon and/or molecular sieve or to a photochlorination step.

According to one embodiment of the invention, the composition is obtained by a series of reactions (FIG. 1). FIG. 1 illustrates a series of reactions for the production of HFO-1234yf. The series of reactions begins with a hydrofluorination reaction of HCC-240db with hydrogen fluoride to give HCFO-1233xf. The compound HCFO-1233xf may in turn undergo a hydrofluorination reaction to give HFO-1234yf. The compound HFO-1234yf may in turn undergo a hydrofluorination reaction to give HFC-245cb. Multitudes of products may be obtained by reactions parallel to this series of reactions for example by isomerization reactions, HCl addition reactions and chlorination reactions.

The reactions described above are preferably carried out in the presence of a supported or unsupported fluorination catalyst, preferably activated in the presence of hydrogen fluoride and/or air, comprising chromium oxides and optionally a co-catalyst based for example on nickel, zinc, titanium, magnesium and tin.

The hydrofluorination reaction(s) may be carried out in the gas phase, optionally in the presence of a sufficient amount of oxygen.

The production of HFO-1234yf may be carried out in one or more reactors in series. The supply of HCC-240db may be placed at the inlet of one of the reactors or at the inlet of the first reactor in series, or at each of the inlets of each of the reactors in series.

The hydrofluorination reaction(s) may be carried out continuously or semi-continuously.

The production of HFO-1234yf may be preferably carried out at an absolute pressure of between 0.1 and 50 bar, more preferably between 0.3 and 15 bar.

The contact time in the reactor is between 1 and 100 seconds, preferably between 5 and 50 seconds.

The molar ratio between the hydrogen fluoride and the organic compounds is between 4:1 and 100:1, preferably between 5:1 and 50:1.

The compositions described according to the invention may contain HF, HCl and inert gases (nitrogen, oxygen, carbon dioxide, carbon monoxide, etc).

HF and HCl neutralization/elimination steps may also be carried out. The compositions described according to the invention may also contain no, or contain traces of, HF and/or HCl.

In the presence of a large excess of HF used in the reaction step(s), the manufacture of HFO-1234yf may comprise at least one distillation step in order to recover a portion of HF that can be recycled to the reaction step(s).

The compositions according to the invention are of use in many fields of application, especially as heat transfer fluid, propellants, foaming agents, blowing agents, gaseous dielectrics, monomer or polymerization medium, support fluids, agents for abrasives, drying agents and fluids for energy production units.

The invention claimed is:

1. A composition comprising the compound HFO-1234yf and at least one other additional compound chosen from HCFC-240db, HCC-40, HCFC-114a, HCFC-115, HCFC-122, HCFC-123, HCFC-124, HCFC-124a, HFC-125, HCFC-142, HCFC-143, HCFC-243ab, HCFC-244eb, HFC-281ea, HCO-1110, HCFO-1111, HCFO-1113, and HCFO-1224xe,
   wherein the composition comprises at most 0.5% by weight of all of the additional compound(s), and
   wherein the at least one other additional compound includes HCC-40.

2. The composition as claimed in claim 1, wherein the at least one other additional compound further includes HCFC-115.

3. The composition as claimed in claim 2, wherein the composition further comprises at least one compound chosen from HFC-152a, HCFC-240db, HCFO-1233xf, HCFC-243db, HCFO-1233zd, HCFC-114a, HCFC-122, HCFC-123, HCFC-124, HCFC-124a, HFC-125, HCFC-133a, HCFC-142, HCFC-143, HCFC-243ab, HCFC-244eb, HFC-281ea, HCO-1110, HCFO-1111, HCFO-1113, HCFO-1223xd and HCFO-1224xe.

4. The composition as claimed in claim 1, wherein the composition further comprises at least one compound chosen from HFO-1234ze, HFC-245cb, HFC-245eb, HFC-245fa, HFC-23, HFC-134a, HFC-143a, HFC-236fa, HCFC-244bb, HCFC-244db, HFO-1132a, HFO-1223, HFO-1225zc, HFO-1225ye, HCFO-1232xf and HFO-1243zf.

5. A composition according to claim 1 comprising at least 99% by weight of HFO-1234yf and up to 500 ppm of HCC-40.

6. The composition as claimed in claim 5, wherein the composition comprises up to 50 ppm of HCC-40.

7. The composition as claimed in claim 5, wherein the composition comprises at least 99.5% by weight of HFO-1234yf.

8. The composition as claimed in claim 1, wherein the composition comprises at least 99% by weight of HFO-1234yf.

9. The composition as claimed in claim 1, wherein the composition comprises at least 99.5% by weight of HFO-1234yf.

10. The composition as claimed in claim 1, wherein the composition comprises HFO-1234yf, HCC-40, and at least one compound selected from the group consisting of HFO-1234ze, HCFC-115, HFC-152a, and HFO-1243zf.

11. The composition as claimed in claim 1, wherein the composition further comprises at least one compound chosen from HFO-1234ze, HFC-245cb, HFC-134a, HCFC-115, HFC-152a, HCC-40 and HFO-1243zf.

12. The composition as claimed in claim 11, wherein the composition additionally comprises at least one other additional compound chosen from HCFC-240db, HCFO-1233xf, HCFC-243db, HCFO-1233zd, HCFC-114a, HCFC-122, HCFC-123, HCFC-124, HCFC-124a, HFC-125, HCFC-133a, HCFC-142, HCFC-143, HCFC-243ab, HCFC-244eb, HFC-281ea, HCO-1110, HCFO-1111, HCFO-1113, HCFO-1223xd, HFC-245eb, HFC-245fa, HFC-23, HFC-143a, HFC-236fa, HCFC-244bb, HCFC-244db, HFO-1132a, HFO-1223, HFO-1225zc, HFO-1225ye, HCFO-1232xf and HCFO-1224xe.

13. The composition as claimed in claim 1, wherein the composition further comprises at least one compound chosen from HFO-1234ze, HFC-134a, HCFC-115, HFC-152a and HFO-1243zf.

* * * * *